United States Patent [19]

Dussourd D'Hinterland et al.

[11] 4,389,396
[45] Jun. 21, 1983

[54] IMMUNOSTIMULATING PREPARATIONS BASED ON RIBOSOMAL RNA'S AND A PROCESS FOR THE PREPARATION OF THE RNA'S

[75] Inventors: Lucien Dussourd D'Hinterland; Gerard Normier; Anne-Marie Pinel; Jacques Durand, all of Castres, France

[73] Assignee: Pierre Fabre, S.A., Paris, France

[21] Appl. No.: 293,639

[22] PCT Filed: Dec. 19, 1980

[86] PCT No.: PCT/FR80/00186

§ 371 Date: Aug. 18, 1981

§ 102(e) Date: Aug. 18, 1981

[30] Foreign Application Priority Data

Dec. 21, 1979 [FR] France .................... 79 31442

[51] Int. Cl.$^3$ ................ A61K 39/108; A61K 39/02; C07H 21/02; A61K 31/70
[52] U.S. Cl. ................................ 424/92; 424/180; 424/88

[58] Field of Search ............... 424/92, 180, 88; 536/27–29; 435/92, 172, 270

[56] References Cited

FOREIGN PATENT DOCUMENTS 839893 4/1975 Belgium .
2253499 7/1975 France .
2305990 10/1976 France .
2360314 3/1978 France .
2374911 7/1978 France .
2388563 11/1978 France .

Primary Examiner—Blondel Hazel
Attorney, Agent, or Firm—Maky, Renner, Otto & Boisselle

[57] ABSTRACT

This invention relates to a non-specific immunostimulating preparation for the treatment of immunodeficits, such as those encountered in leprosy and cancer, characterized in that it contains as sole active principle one or more bacterial ribosomal RNA's extracted from the following strains:
Klebsiella pneumoniae
Serratia marcescens

10 Claims, No Drawings

IMMUNOSTIMULATING PREPARATIONS BASED ON RIBOSOMAL RNA'S AND A PROCESS FOR THE PREPARATION OF THE RNA'S

This invention which was developed at the Centre d'Immunologie et de Biologie PIERRE FABRE relates to non-specific immunostimulating preparations containing ribosomal RNA's and to processes for the preparation of these RNA's.

The vaccinating power of ribosomes and RNA's is known but is only developed in the presence of adjuvants, such as membranal proteoglycans or membranal polysaccharides, in addition to which the activity developed is essentially preventative.

Now, the Applicants have found that certain RNA's may be used on their own for the treatment of diseases attributable to immunodeficits, such as leprosy and cancer.

Thus, the Applicants have demonstrated the very considerable non-specific immunostimulating power of the ribosomal RNA's of:

Klebsiella pneumoniae
Serratia marcescens

Accordingly, the present invention relates to non-specific immunostimulating preparations for the treatment of immunodeficits such as those encountered in leprosy and cancer, characterised in that they contain as sole active principle one or more bacterial ribosomal RNA's extracted from the following strains:

Klebsiella pneumoniae
Serratia marcescens

The immunostimulating preparations according to the invention are preferably made up in injectable form, the concentrations and frequency of the injections being of course variable according to the disease to be treated. In the majority of cases, each dose contains of the order of 10 $\mu$g to 50 $\mu$g of ribosomal RNA in a support acceptable in human therapeutics which corresponds to the daily doses for an adult.

The present invention also relates to a process for the preparation of RNA suitable for working on a commercial scale. The processes which have hitherto been described for the preparation of ribosomal RNA's are all based on a complex technology which does not lend itself to large-scale production under satisfactory conditions. Thus, in the process in which the RNA's are extracted with phenol, the extraction phases are difficult to separate with existing industrial apparatus.

Accordingly, the process according to the present invention is a process for the preparation of bacterial ribosomal RNA's which is characterised in that:

(a) the ribosomes are separated from the ground bacteria, (b) the crude RNA is extracted from the ribosomes by mixing the ribosomes with an aqueous solution of sodium dodecyl sulphate under heat and precipitating the crude RNA's, and (c) the crude RNA is treated with at least one proteolytic enzyme under heat, followed by precipitation of the purified RNA's.

In one preferred embodiment, this process is characterised in that:

(a) the ribosomes are separated from the ground bacteria by centrifuging, (b) the crude RNA is extracted from the ribosomes by mixing the ribosomes with an aqueous solution of sodium dodecyl sulphate having a concentration of from 1 to 5% at a temperature in the range from 30° to 50° C., the crude RNA's are precipitated by adding sodium acetate and ethanol to the mixture and collecting the precipitate of crude RNA's, (c) the crude RNA is treated with a proteolytic enzyme at a temperature in the range from 20° to 40° C., after which the purified RNA is precipitated by adding ammonium cetyl trimethyl bromide to the solution obtained, the precipitate of purified RNA's is collected and the ammonium cetyl trimethyl bromide is eliminated from the precipitate.

The treatment with sodium dodecyl sulphate enables the majority of proteins attached to the RNA by ionic bonds to be liberated. The treatment with proteolytic enzymes enables the proteins remaining after the preceding treatment to be eliminated by cleavage.

In one preferred embodiment of the process, a 2.5% solution of sodium dodecyl sulphate (SDS) is used for about 30 minutes at a temperature of +40° C.

After precipitation of the crude RNA's, it is of advantage to repeatedly wash the deposit of RNA with aqueous ethanol containing sodium acetate before exposing it to the action of the proteolytic enzyme.

Proteolytic enzymes suitable for use in accordance with the invention include in particular pronase and trypsin.

The proteolysis mixture is treated with a solution containing from 2 to 10% by volume of ammonium cetyl trimethyl bromide (CETAVLON), the precipitate being recovered by centrifuging.

The RNA may be recovered from the precipitate by washing the deposit with an excess of aqueous ethanol containing sodium acetate which enables the CETAVLON to be eliminated.

The processes by which the ribosomes are prepared from ground bacteria are known, cf. for example French Pat. No. 75 10252 in the name of the Applicants.

Preferably, the bacterial suspension is ground, after which the bacterial lystate is clarified by centrifuging under an acceleration of from 10,000 to 50,000 G to obtain a clear supernatant phase.

Grinding may be carried out by means of Manton Gaulin APV homogenisers equipped with special disintegration valves or glass microbead dispersers of the Dyno-Mill or similar type.

The supernatant phase is treated with DNase, after which the ribosomes are precipitated with ethanol at a low temperature (of the order of −10° to −30° C.). The precipitate may be collected by centrifuging.

To obtain an extremely pure RNA, the purified RNA's are taken up in a 0.05 M tris-HCl buffer (pH 7.2) and chromatographed in a column of DEAE cellulose by an NaCl gradient. Highly pure RNA's are obtained in this way.

The purified or highly purified RNA obtained may be sterilised and preserved by freezing or freeze-drying.

The present invention obviously relates to the non-specific immunostimulating preparations containing RNA's obtained by the process described in the foregoing, although they may also be obtained by other processes.

The invention also relates to the RNA's obtained by the process described above.

The following Example is intended to illustrate one embodiment of the process according to the invention for the purpose of illustrating certain characteristics thereof without limiting it in any way.

EXAMPLE 1

The bacterial cells of *Klebsiella pneumoniae* type 1 are obtained by a conventional fermentation process and then concentrated by continuous centrifuging in separators of the Sharples or Westfalia type. The biomass is then washed with physiological serum and reconcentrated by continuous centrifuging. The bacterial concentrate thus obtained is subjected to the usual bacteriological examinations and to determination of its dry extract content. It is stored frozen at low temperature.

The bacterial concentrate is suspended in a 0.01 M pH 7.0 solution of $MgCl_2$ at $+4°$ C. so as to obtain 5 g of dry extract in 100 ml of suspension.

The bacterial suspension is subjected to grinding in a Manton Gaulin APV homogeniser intended to break the cell walls and to release the cytoplasmic content. This operation is carried out at a temperature kept below 10° C. by means of a heat exchanger installed in the circuit.

The bacterial lysate is then clarified by centrifuging for 45 minutes at 30,000 G at low temperature. The residue is eliminated and the clear supernatant phase is collected.

The supernatant phase is treated for 1 hour at 30° C. while stirring with DNase strictly free from ribonuclease and then cooled to $+4°$ C.

The ribosomes are immediately precipitated by the addition of 0.7 volumes of ethanol at $-20°$ C. After standing for 30 minutes at $+4°$ C., the precipitate is collected by centrifuging and the supernatant phase eliminated.

The deposit of crude ribosomes is taken up in a 2.5% solution of SDS at $+40°$ C. and the RNA is extracted for 30 minutes with rapid stirring at that temperature.

The RNA is then precipitated by the addition of sodium acetate, QSP 0.2 M, and then 0.8 volume of ethanol at $-20°$ C. After standing for 30 minutes at $+4°$ C., the precipitate is collected by centrifuging and the supernatant phase is eliminated.

The deposit is washed twice with an excess of ethanol (70%) containing 0.1 M $CH_3COONa$ and is then taken up in concentrated solution in 0.05 M pH 7.0 tris-HCl buffer.

The residual proteins which may still be present with the RNA are eliminated by treatment for 1 hour at 30° C. with pronase (or trypsin) followed by cooling to $+4°$ C.

The RNA is precipitated from this solution by the progressive addition of 0.5 volume of a 5% aqueous solution of CETAVLON (ammonium cetyl trimethyl bromide) at $+4°$ C. After standing for 5 minutes, the RNA-CETAVLON precipitate is collected by centrifuging and the supernatant phase eliminated.

The deposit is washed three times with an excess of 70% ethanol containing 0.2 M pH 7.0 $CH_3COOONa$, followed by centrifuging. The effect of this is to convert the RNA into soluble sodium salt and to eliminate the CETAVLON.

The thoroughly centrifuged deposit of RNA is taken up in 0.05 M pH 7.2 buffer and then purified by chromatography in a column of DEAE cellulose. The RNA retained in this column is eluted in the form of a highly purified RNA peak by an NaCl gradient (0 to 0.5 M) in the same buffer.

The fraction containing the purified RNA is collected, dialysed against distilled water and then sterilised by filtration.

The RNA thus obtained by may be stored frozen at low temperature or even in freeze-dried form.

Analytical Methods Used for Examining the RNA Preparations:

The RNA is determined by three methods:
(1) Direct spectrophotometric determination at 256 nm by comparison with a standard commercial preparation.
(2) Determination of the phosphorus content knowing that pure ribosomal RNA contains 8.2% of phosphorus (Fiske and Subbarow, J. Biol. Chem. (1926), 66, 375).
(3) HPLC chromatography using an ion exchange column after hydrolysis for the qualitative and quantitative assessment of the composition as formed by purine and pyrimidine bases and detection of the thymine characteristic of DNA.

EXAMPLE 2

This Example is intended to demonstrate the therapeutic effect of a ribosomal RNA preparation of *Klebsiella pneumoniae* prepared by the process of Example 1.

This experiment is conducted on Lewis tumours in C57 B1/6 mice. The animals are given 5, 10 or 15 μg of ribosomal RNA of *Klebsiella pneumoniae* type 1 three times weekly at the same time as a series of controls. The treatment begins on the day the tumoral cells are injected and is continued to the death of the animals.

The criteria collected are as follows:
(1) time of appearance of the tumour,
(2) survival,
(3) weight, volume and surface area of the tumour,
(4) weight of the thymus and the spleen,
(5) weight of the lungs and number of pulmonary metastases.

The results are set out in the following Table:

| Criterion measured | 7th day | 14th day | 21st day | 28th day |
| --- | --- | --- | --- | --- |
| Weight of the tumours (g) | | | | |
| controls | 1.79 | 3.18 | 8.364 | 11.987 |
| treated | 1.71 | 2.139 | 4.485 | 7.368 |
| Volume of the tumours (ml) | | | | |
| controls | 1.58 | 3.0 | 8.79 | 11.83 |
| treated | 1.723 | 2.196 | 3.93 | 6.01 |
| Surface area of the tumours (cm$^2$) | | | | |
| controls | 32.4 | 110.33 | 164.33 | 765 |
| treated | 30.27 | 41.56 | 149 | 169 |
| Weight of the spleen (g) | | | | |
| controls | 0.1333 | 0.1665 | 0.1903 | 0.1926 |
| treated | 0.1189 | 0.1206 | 0.1954 | 0.3456 |
| Weight of the thymus (g) | | | | |
| controls | 0.0472 | 0.0339 | 0.0047 | — |
| treated | 0.0591 | 0.0442 | 0.0206 | 0.0110 |

What is claimed is:
1. A process for the preparation of bacterial ribosomal RNA comprising:
    (a) providing a ground bacterial suspension;
    (b) separating ribosomes from said suspension;
    (c) extracting crude RNA from the separated ribosomes by mixing said ribosomes with an aqueous solution of sodium dodecyl sulfate and precipitating crude RNA; and

(d) treating said crude RNA with at least one proteolytic enzyme and precipitating the treated RNA.

2. The process of claim 1 wherein the ribosomes are separated from the suspension in step (b) by centrifuging.

3. The process of claim 1 wherein the sodium dodecyl sulfate used in step (c) has a concentration of from 1 to 5% and a temperature in the range of 30° to 50° C.

4. The process of claim 1 wherein the crude RNA precipitated in step (c) is precipitated by adding sodium acetate and ethanol to the mixture.

5. The process of claim 1 wherein the treatment of the crude RNA with proteolytic enzyme in step (d) is at a temperature in the range of 20° to 40° C.

6. The process of claim 1 wherein the treated RNA is precipitated in step (d) by adding ammonium cetyl trimethyl bromide to the solution.

7. The process of any of claims 1–6 wherein the treated RNA is taken up in a 0.05 M tris-HCl buffer and chromatographed in a column of DEAE cellulose by a sodium chloride gradient.

8. A method of treating diseases attributable to immunodeficits with a non-specfic immunostimulating preparation comprising:

provideing a non-specific immunostimulating preparation characterized by the absence of adjuvants comprising bacterial ribosomal RNA extracted from *Klebsiella pneumoniae* or *Serratia marcescens* as the sole active principle and a therapeutically acceptable support; and administering an effective amount of said preparation to the patient being treated.

9. The method of claim 8 wherein said non-specific immunostimulating preparation is provided in an injectable form.

10. The method of claims 8 or 9 wherein each dose of said non-specific immunostimulating preparation contains from 10 to 50 μg of RNA.

* * * * *